（12）United States Patent
Lee (10) Patent No.: US 8,869,792 B1
(45) Date of Patent: Oct. 28, 2014

(54) PORTABLE VAPORIZER

(76) Inventor: Chung Ju Lee, Glendora, CA (US)

( * ) Notice: Subject to any disclaimer, the term of this patent is extended or adjusted under 35 U.S.C. 154(b) by 568 days.

(21) Appl. No.: 13/188,450

(22) Filed: Jul. 21, 2011

Related U.S. Application Data (60) Provisional application No. 61/366,603, filed on Jul. 22, 2010.

(51) Int. Cl.
*A61M 15/06* (2006.01)

(52) U.S. Cl.
USPC ............. 128/202.21; 128/203.15; 128/203.27

(58) Field of Classification Search
CPC ............. A61M 15/06; A61M 11/041; A61M 2205/3653; A61M 2205/3368; A61M 2205/8206
USPC ............. 128/202.21, 200.11, 200.12, 200.14, 128/200.16, 200.18, 200.21, 200.24, 128/203.12, 203.15, 203.16, 203.17, 128/203.26, 203.27, 204.18, 204.21
See application file for complete search history.

(56) References Cited

U.S. PATENT DOCUMENTS

| | | |
|---|---|---|
| 2,104,266 A | 1/1938 | McCormick |
| 4,141,369 A | 2/1979 | Burruss |
| 4,206,770 A | 6/1980 | Ozgener |
| 5,144,962 A | 9/1992 | Counts et al. |
| 5,249,586 A | 10/1993 | Morgan et al. |
| 5,598,835 A | 2/1997 | Von Schrader |
| 5,687,777 A | 11/1997 | Dobson |
| 5,865,185 A | 2/1999 | Collins et al. |
| 6,513,524 B1 | 2/2003 | Storz |
| 6,772,756 B2 | 8/2004 | Shayan |
| 7,186,958 B1 | 3/2007 | Nelson |
| 2006/0283449 A1 | 12/2006 | Balch |
| 2008/0023003 A1 | 1/2008 | Rosenthal |
| 2008/0191153 A1 | 8/2008 | Marganski |
| 2009/0078253 A1 | 3/2009 | Bao |
| 2009/0302019 A1 | 12/2009 | Selenski |
| 2010/0322599 A1 | 12/2010 | Landry |
| 2011/0126831 A1 | 6/2011 | Fernandez |

*Primary Examiner* — Melanie Hand
*Assistant Examiner* — Aundria Hairell
(74) *Attorney, Agent, or Firm* — Law Office of David Hong (57) ABSTRACT

A portable apparatus for vaporizing herbs and plants comprising a housing or mixing chamber, which incorporates a vaporizing/heating element and a rotatable mixing element that allows for an effective level of mixing of the heated plants and the herbs during the vaporization process.

5 Claims, 12 Drawing Sheets

PORTABLE VAPORIZER

BACKGROUND OF THE INVENTION

This application claims the benefit of U.S. Provisional Patent Application No. 61/366,603, filed Jul. 22, 2010, which is incorporated by reference.

1. Field of the Invention

This invention relates to a portable vaporizer.

2. Description of Related Art

The traditional method of smoking tobacco, herbs and plants (other than rolling the dried herbs and plants into a cigarette) uses a Hooka-style device or a bong-style apparatus. Other types of herbs can be used in these apparatus.

True connoisseurs of herbs prefer not to burn the herbs, but rather use vaporization, which is accomplished by heating the herb/plant up to the temperature, whereby the desired chemical (e.g. nicotine) starts vaporizing and avoids creating other non-desirable chemicals generated through burning, such as carbon monoxide or carbon dioxide and other carcinogens. There is a list of herbs and their vaporization temperature shown at the following Internet Website: http://en.wikipedia.org/wiki/Vaporizer.

A typical desktop vaporizer heats up a volume of air to the desired temperature and when the user inhales, the heated air passes through the herb to cause vaporization of the desired chemical. These vaporizers require plugging into the wall outlet, and contain a heating element that can be heated up to 200 degrees Celsius (some higher). The high temperature is required because air is a poor conductor of heat. In order to raise the air to approximately 200 degrees Celsius, a much higher temperature is required from the heater to account for this inefficiency.

Recently, manufacturers have been coming up with portable vaporizers that heat up the herb directly, instead of heating a volume of air. This helps to lower the temperature of the heater to the required temperature for "just" vaporization. The method for heating can be by liquid fuel (e.g. butane) such as the "Iolite" brand portable vaporizer. The fire created heats up a heat-conductive crucible that contains the herb. The other way is by electric means such as the "Vapir" brand vaporizer, whereby batteries (typically high-density lithium) power a heating element or coil that is in contact with the herb.

The inherent drawback of portable heaters is that herb itself is a poor conductor of heat. The section of the herbs that is in direct contact with the heating element can reach vaporization temperature quickly, but the rest of the leaves are often too cold to vaporize. Very often, the user has to wait a long time in order to get enough vapors to get their "kick," or otherwise inhale multiple times just to match the effect of a desktop vaporizer.

In order to create enough vaporization, some electric portable vaporizers use larger heaters so that more leaves are in contact, but larger heaters require more power, thereby shortening the battery life. Users can also open up the container lid to manually stir the herb in order to mix up the burned and unburned herb, but this is inconvenient, and "precious" vapors will be lost every time the lid is opened.

From the preceding descriptions, it is apparent that the devices currently being used have significant disadvantages. Thus, important aspects of the technology used in the field of invention remain amenable to useful refinement.

SUMMARY OF THE INVENTION

A portable apparatus for vaporizing herbs and plants comprises a housing or mixing chamber, which incorporates a vaporizing/heating element and a mixing element; this mixing element allows for an effective level of mixing of the heated plants and herbs during the vaporization process. This invention also combines a mixing element that works in conjunction with the vaporizing or condensing element so that an efficient level of extraction of desired volatile materials is achieved at a lower use of energy.

The present invention introduces such refinements. In its preferred embodiments, the present invention has several aspects or facets that can be used independently, although they are preferably employed together to optimize their benefits. All of the foregoing operational principles and advantages of the present invention will be more fully appreciated upon consideration of the following detailed description, with reference to the appended drawings.

PARTS LISTING:

10 apparatus
12 housing
15 vaporizing chamber (glass tube, which has the mixing element and the vaporizing/heating element)
20 glass tube of vaporizing chamber
22 glass tube holder
25 mixing or stirring element 27 heater or heating element
30 condenser
35 crucible (within condenser cap)
40 condenser cap
45 wire mesh end of condenser cap
50 bowl cap
55 mouthpiece
60 filter
65 stirring wheel (spins vaporizing and stirring elements)
67 roller
70 temperature dial
80 battery or power source
85 activation button for power
90 charging jack port for battery
95 heater on/off button
100 housing

DESCRIPTION OF THE PREFERRED EMBODIMENTS

Figure 1:
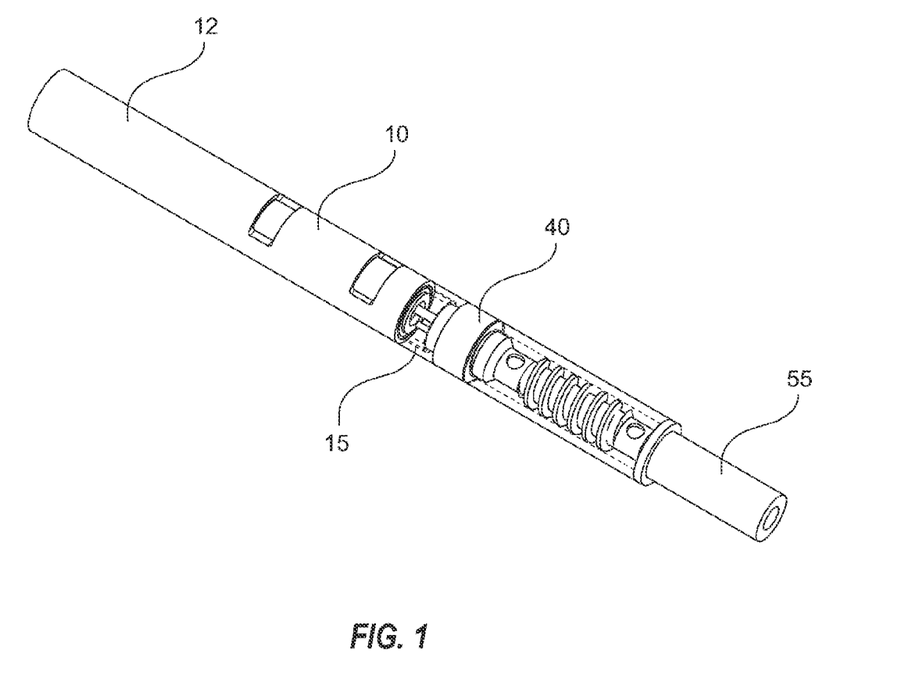
FIG. 1 is a perspective view of the vaporizing apparatus with the cooling unit attachment.
Figure 2:
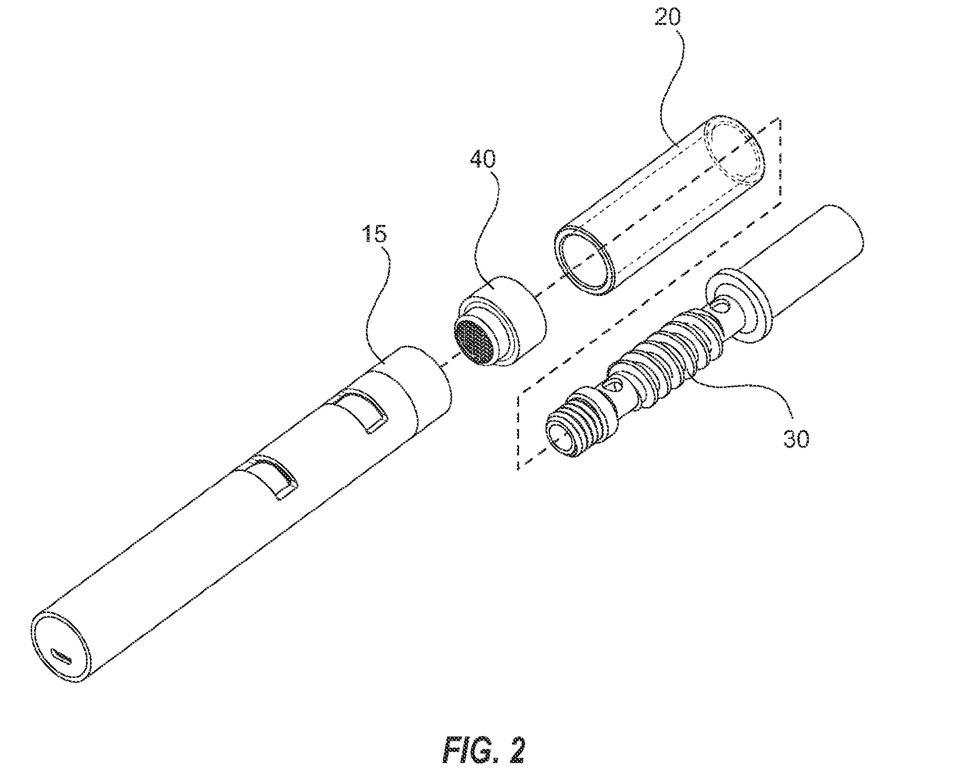
FIG. 2 is an exploded view of the vaporizing apparatus with the cooling unit attachment as shown in FIG. 1.
Figure 3A:
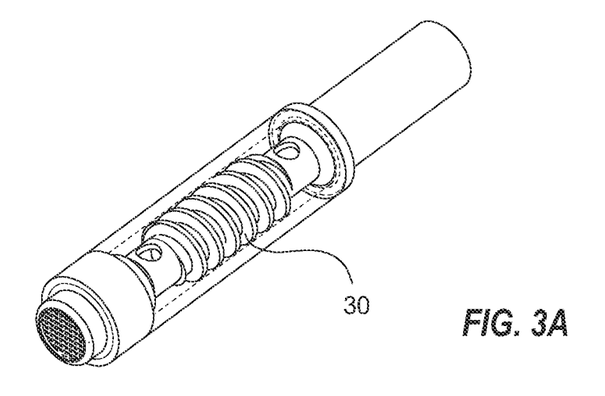
FIG. 3A, FIG. 3B and FIG. 4 respectively show a perspective view, an exploded view and a cross-sectional view of the cooling unit attachment.
Figure 3B:
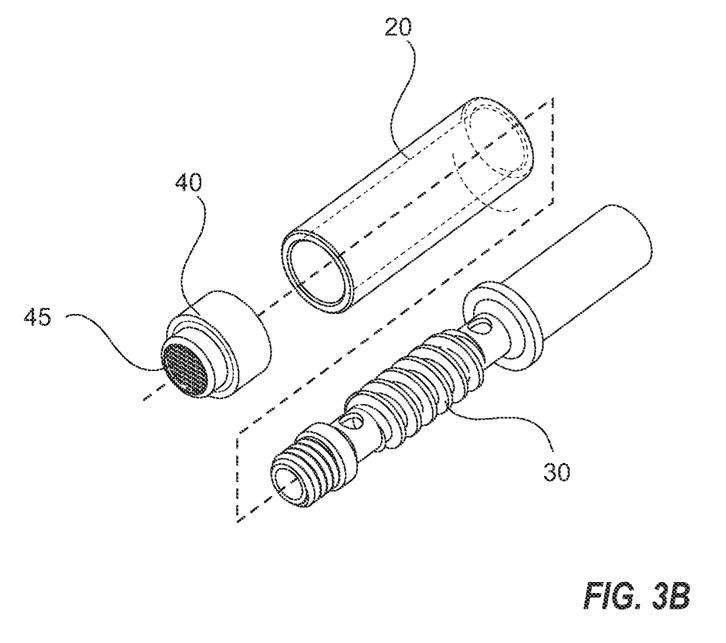
Figure 4:
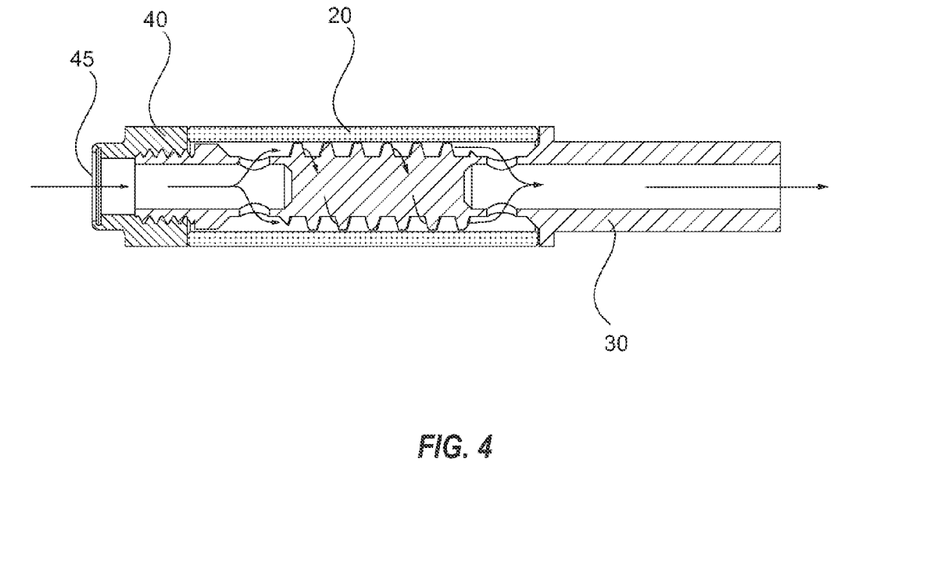
Figure 5:
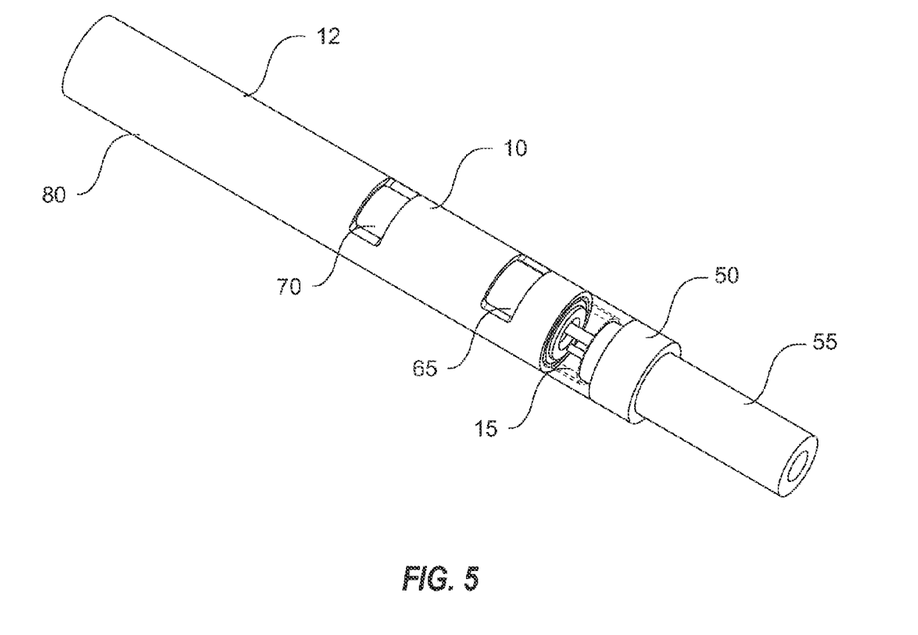
FIG. 5 and FIG. 6 are respectively top and bottom perspective views of the vaporizing apparatus with the vaporization chamber with a heating or vaporizing element, a stirring element and a glass chamber. There is also a bowl cap, filter and a mouthpiece. The housing also has a space for a battery or other power source (gas, butane, etc.), a temperature dial, activation buttons and a manually operated stirring wheel.
Figure 6:
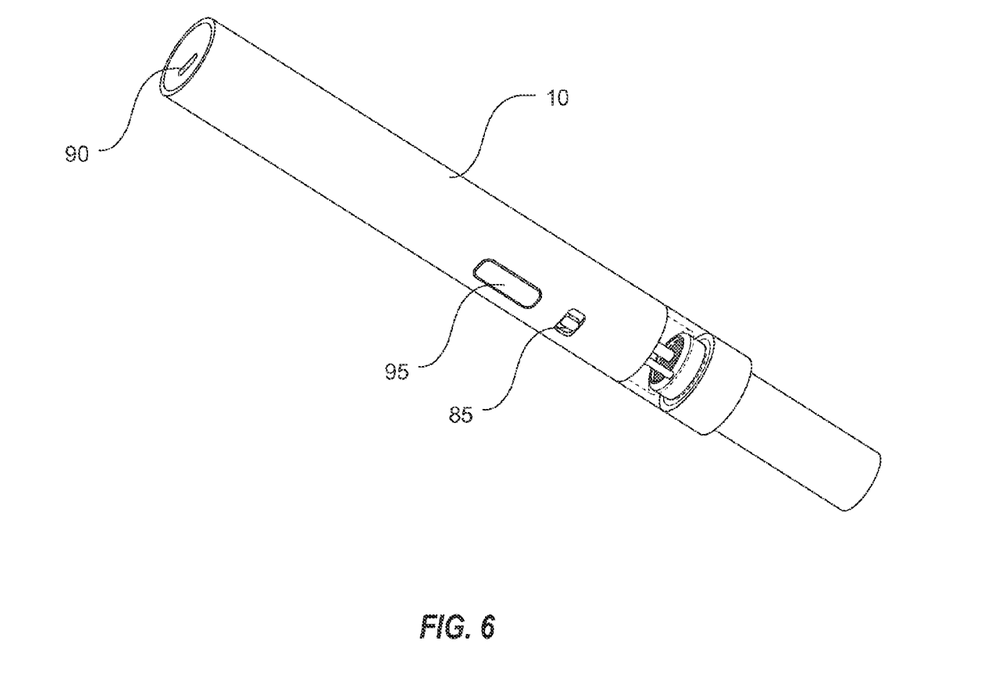

A portable apparatus for vaporizing herbs and plants comprising a vaporizing chamber that has a vaporizing element and a mixing element that allows for an effective level of mixing of the herbs during the vaporization process. There can also be a condenser or cooling chamber attachment. FIG. 1-2 show views of the vaporizing apparatus with the cooling or condenser attachment.

Figure 7:
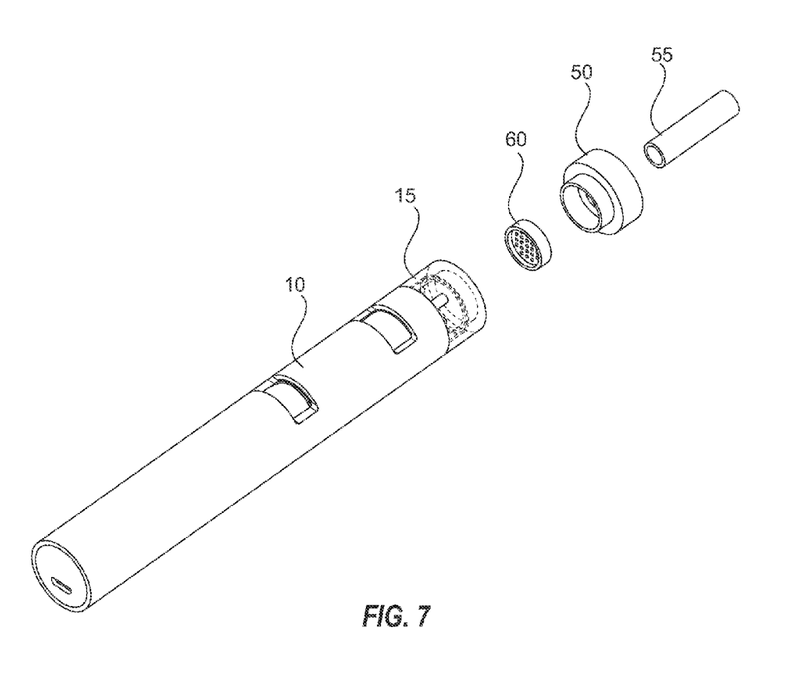
FIG. 7 is an exploded view of the vaporization apparatus, including the vaporization chamber, filter, bowl cap and the mouthpiece.
Figure 8:
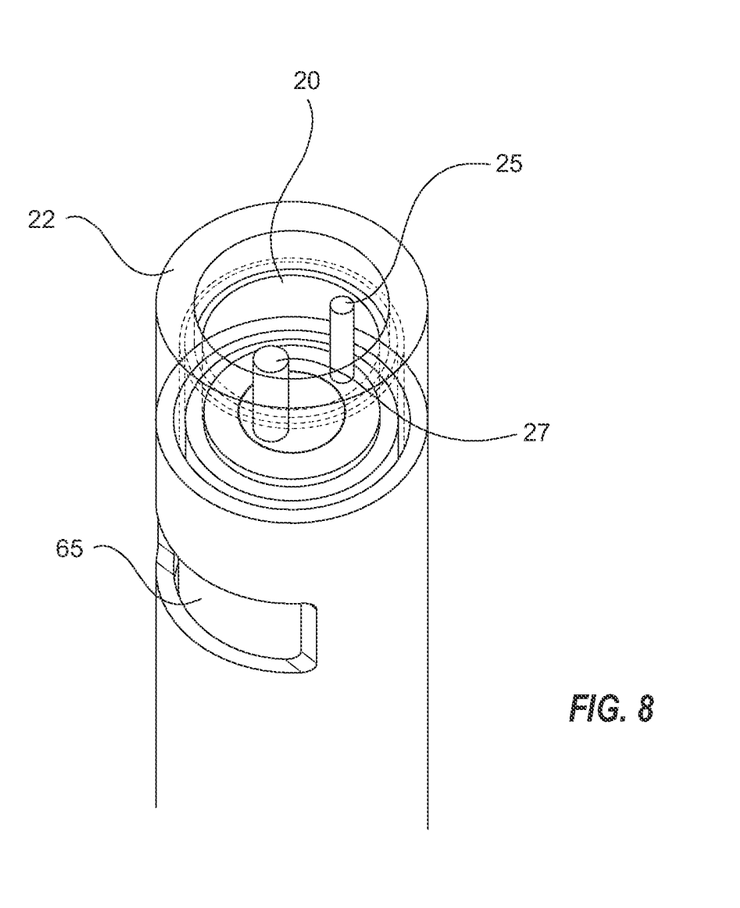
FIG. 8 is a perspective view of one embodiment of the vaporizing chamber or glass tube, which is surrounded by a transparent outer housing or a glass tube holder; there is also a ceramic rod heating element and a stirring element and a stirring wheel.
Figure 9:
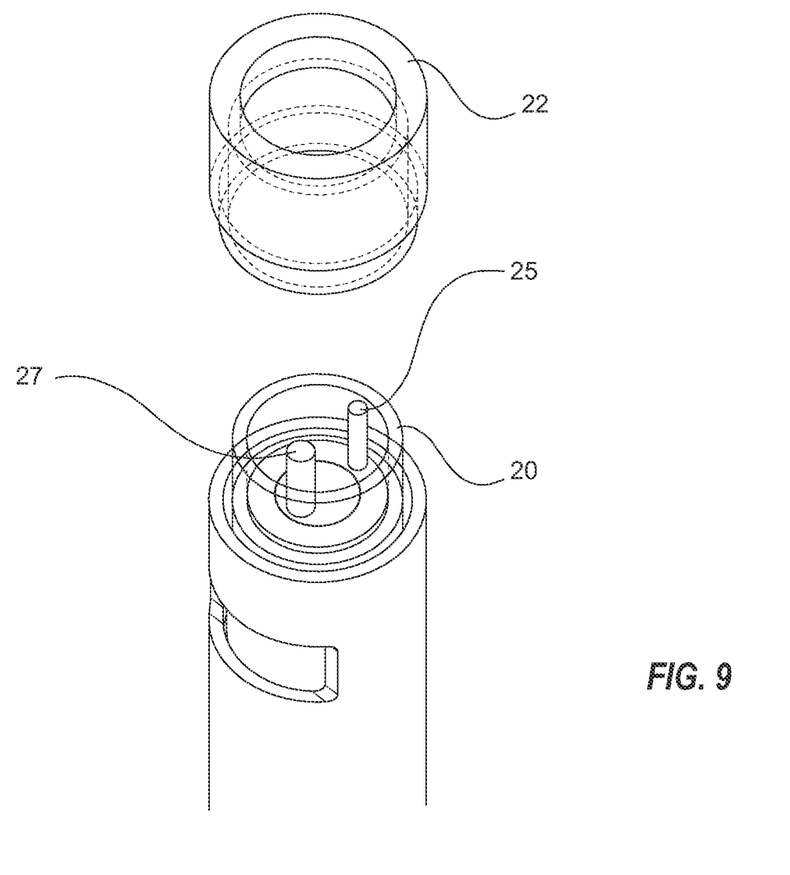
FIG. 9 is a view of the invention with the glass tube holder removed.

Vaporizing Apparatus:

In FIG. 5 to FIG. 10B, there is a vaporizing apparatus with a first end and a second end. The first end has a mouthpiece portion and a vaporizing chamber. In FIG. 8, the vaporizing chamber has an inner compartment or tube, which is preferably glass, a mixing element and a heating (or vaporizing) element. Surrounding the circumference of the glass tube or inner compartment of the vaporization chamber, there is an glass tube holder, which can be made of transparent plastic for insulation and for viewing the herbs.

Depending on the particular embodiment, either or both of the heating/vaporizing element and mixing element can be moveable, rotatable or rotating.

On one side of the vaporizing chamber is a mouthpiece end, which comprises: a bowl cap, a mouthpiece and a filter. The mouthpiece end is removable from the main apparatus and the vaporizing chamber. In FIG. 7, the filter for the mouthpiece apparatus helps keep the herbs within the vaporizing chamber and out of the mouthpiece area. The filter is perforated with openings or slits to allow the vapors of the heated plants and herbs to pass through to the mouthpiece and to the user's mouth.

In another embodiment, the filter can be composed of fiber-like materials (as a substitute or in combination with the perforated filter) to reduce the chance of uneven rate of vapor into the mouthpiece apparatus. The filter can lie within the bowl cap; one end of the bowl cap engages the first end of the vaporizing chamber.

In FIG. 8, there is a perspective view of the vaporizing chamber. In FIG. 5-9, one preferred embodiment has a housing with the mouthpiece apparatus and the vaporizing chamber at one end. The housing also contains a power source and at least one activation button. Other embodiments can include a temperature gauge or indicator, a heating on/off button, a main power switch and direct current access jack for a rechargeable battery.

The location of these components can be moved based on the shape of the housing. In the attached figure pages, the housing is primarily an elongated tube, but other shapes such as rectangular or other geometric shapes or irregular shapes can be used for the housing.

This housing can have several layers. The outermost layer can be made of any plastic, metal, bamboo, wood, or any durable material; this outermost layer can also be transparent. At the vaporization chamber and within this outermost layer (or glass tube holder), there is the glass tube of the vaporizing chamber. Since the vaporizing chamber and glass tube can get hot during use, the glass tube holder, which is typically made of plastic, acts as an insulating and protective layer around the vaporizing chamber.

Figure 12A:
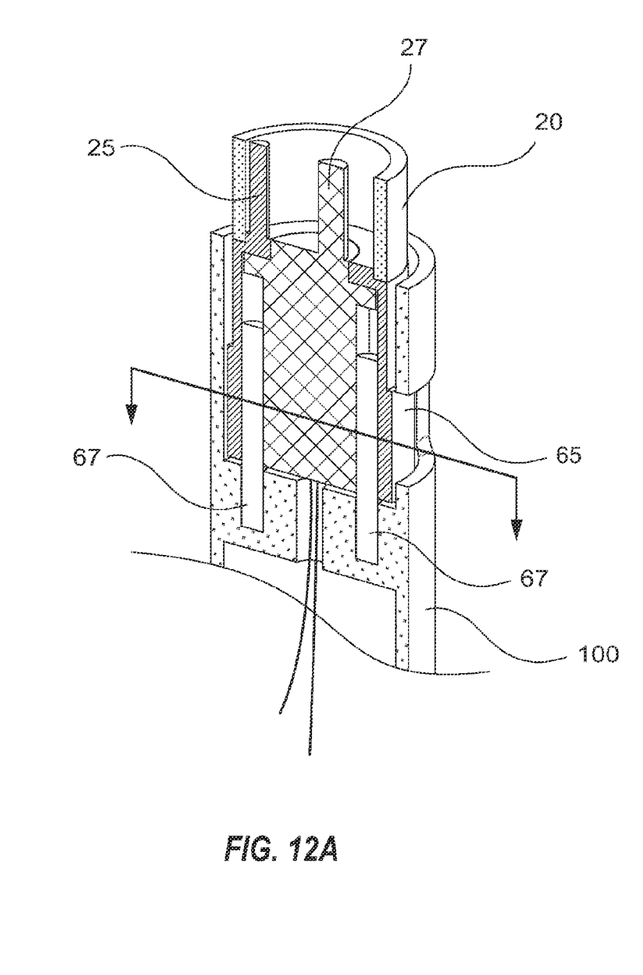
FIG. 12A shows a cross-sectional views of the first end of vaporizing unit, including an embodiment with one stir element and a heater.
Figure 12B:
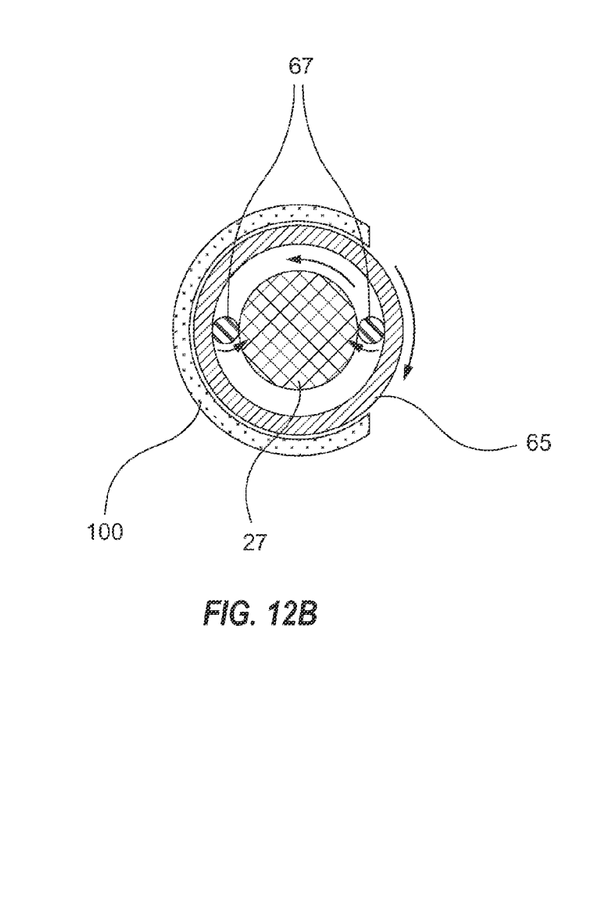
FIG. 12B shows a view along the sight line as shown in FIG. 12A.

Mixing Element:

As shown in FIG. 8 to FIG. 12A and FIG. 12B, the mixing or stirring element can be metal or ceramic material, and the mixing element is attached to or part of the stirring wheel. As shown in FIGS. 12A and 12B, the stirring element has a first stirring element end and a second stirring element end; the first stirring element end or mixing rod is preferably within the vaporization chamber and contacts the plants or herbs to be mixed; the second stirring element end engages at least one roller and also can be manipulated by hand or motor to allow rotation or movement (commonly through an opening in the housing). FIGS. 12A and 12B employ two rollers or bearings in between the centrally located heating element and the outer located stirring element or elements.

The user can access the stirring wheel through a window opening in the outer housing to rotate the wheel or via a movement button, which is connected to the second end of the stirring element. When the user rotates or moves the stirring wheel with a finger or via a motor, this motion will move the attached stirring element rod to mix the herb within the vaporization chamber. Other embodiments allow for a small motor to rotate or to move the stirring element.

Within the stirring wheel radius, there can be at least one turning wheel, which helps rotate the heating rod element in a preferably opposite direction. In the preferred embodiment, there will be two turning wheels. See the first embodiment in FIG. 10B, FIGS. 12A and 12B, the heater and stirrer portions will spin in opposite directions to most efficiently mix the herb to be vaporized. More than one heating element or stirring element can be used.

In FIG. 12B, one can see the interaction when the stirring wheel is rotated by the finger of the user (through the opening in the housing), the at least one internal roller will also rotate the heating element.

Figure 10A:
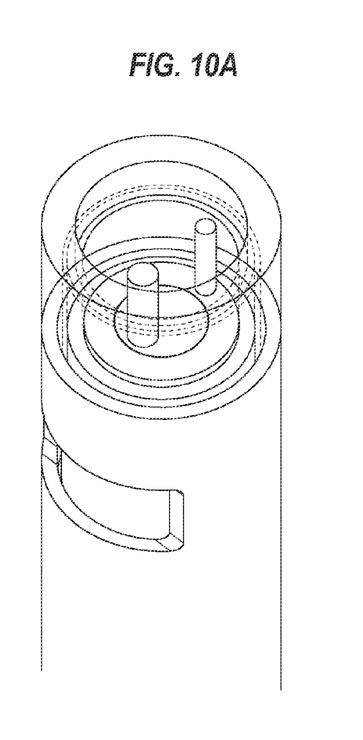
FIG. 10A is a close up view of one end of the vaporizing chamber.
Figure 10B:
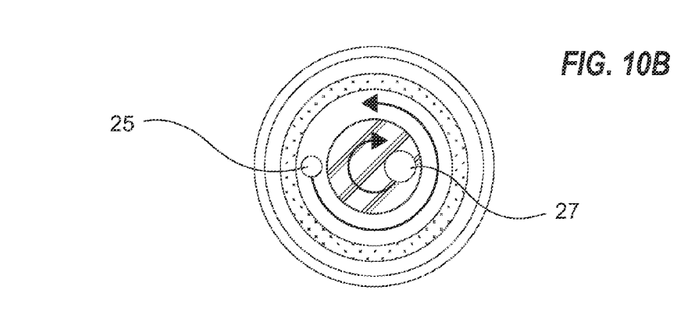
FIG. 10B and FIG. 10C also show alternative embodiments of the heating and stirring elements, which are rotating or moving in opposite directions, along the same axis or along different parallel axis. The rods can be heating or stirring elements; also, the glass tube itself can also be a heating element in FIG. 10C.
Figure 10C:
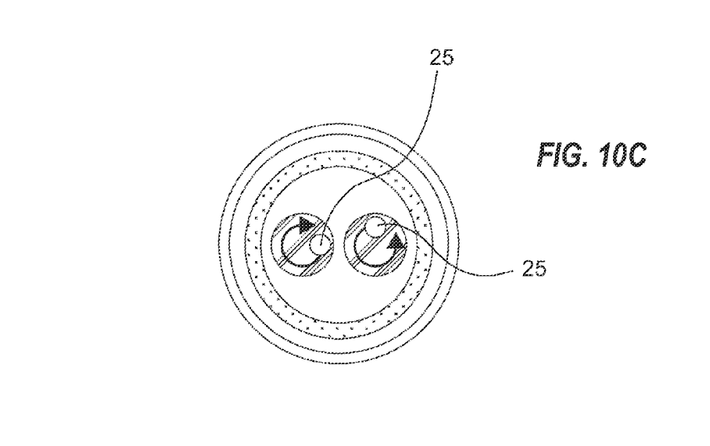
Figure 11A:
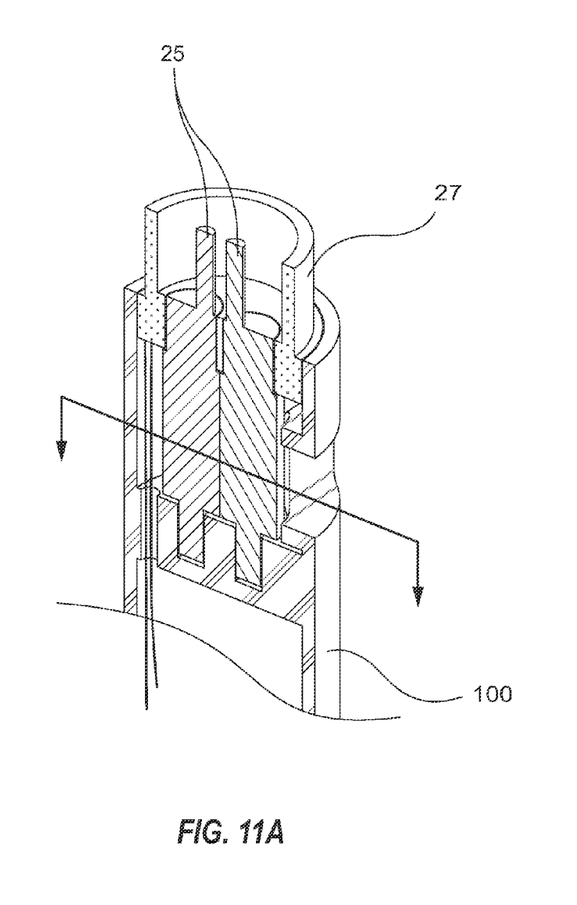
FIG. 11A shows a cross-sectional view of the first end of vaporizing unit, including an embodiment with two stir elements and a heater.
Figure 11B:
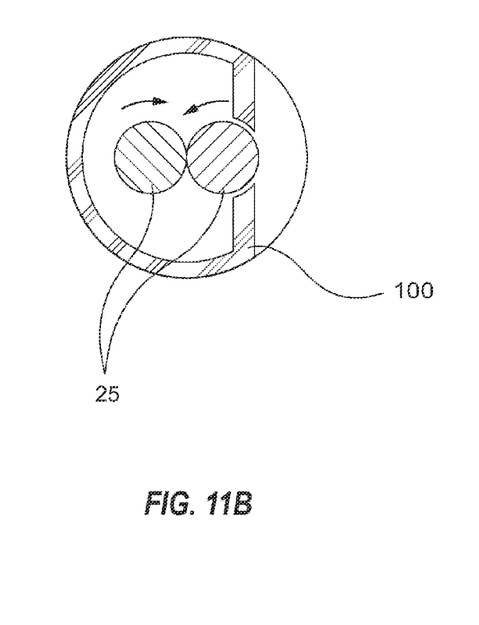
FIG. 11B shows a cross-section view along the sight line as shown in FIG. 11A.

In another embodiment in Fig. Pages 10C and FIGS. 11A and 11B, the two inner rotating wheels can both be stirring wheels, and the glass chamber itself can act as the heating element, since glass is a good conductor of energy; the two inner rotating wheels preferably rotate in opposite directions.

The inventor has considered incorporating a single stirring apparatus that spins in the container, but since the herb is not a fluid, it simply spins along with the stir, and the leaves do not get mixed. It is possible to have this single stir mechanism; however, in order to better mix the leaves, this invention uses bi-directional stir elements and/or a movable heating element with the stir element to create the "tumbling" effect.

Another way to explain this effect of "tumbling" is to ensure that the distance between the stir elements relative to the container is always changing (similar to how a kitchen blender or mixer works). This can be helped with multiple rods that turn counter clockwise around a common axis or counter-clockwise along a different but parallel axis. Another possible version may have a square or rectangular shaped glass vaporizing chamber in combination with a circular stir element.

In another embodiment, the first end of the stir element can also have small paddles, ridges, protrusions, fins or bosses to help move the herbs and plants within the vaporization chamber.

Heating Element:

The heating element can be stainless steel, a ceramic rod heater or even the glass housing itself. The heating element can be powered via a battery, a rechargeable battery (including a DC outlet) or other suitable means (including gas); there can also be a temperature indicator or dial and activation buttons associated with the heating element.

Condenser Apparatus or Attachment:

The condenser apparatus is an attachment, which can be placed between the mouthpiece and the bowl cap or a condenser cap. In another possible embodiment, the condenser apparatus can be directly attached to the vaporization chamber. The condenser apparatus can be in addition to the filter. In FIG. 1-2, this embodiment of the invention has the mouthpiece as a part of the condenser attachment.

At the first end of the condenser apparatus, there is a condenser cap and a wire mesh to keep the herbs from falling out of the vaporizing chamber; the condenser cap will engage the glass tube and one end of the condenser.

The condenser apparatus has a glass or plastic body, and within the glass or plastic body, there is a condenser module, which can have a threaded body and a first condenser end and a second condenser end. The first condenser end can be threaded and hollow and has at least one hole or opening to allow the vapors to pass through and to the threads or waves of the condenser module. Since there is much exposed material of the threads or wave of the condenser, the temperature of the vapor will be reduced. The second condenser end acts as a mouthpiece. The user can add an additional mouthpiece extension to the second end of the condenser.

One of the advantages of using this condenser module is to increase the amount of the vapor produced during one session. In a typical portable bong-style apparatus, the amount of vapor is limited by the inside of the burning chamber. Quite differently, in the instant invention, this condenser module enables a greater storage space for the vapor to collect for one inhalation.

The coolant module can also be considered as an extension to be added to the bowl cap that incorporates a "coolant" apparatus. This coolant apparatus can be a heat-conductive (absorbing) material such as steel, aluminum or ceramic. This allows the vapors to be cooled before inhalation. Prior art bong-style devices have a big "storage" capacity to which users sometimes add ice to chill or cool the collected vapor.

For a portable vaporizer, one preferred way is to pass the vapor over a colder material to absorb the heat. By incorporating threads on the coolant, it extends the distance the vapor has to travel from the inlet to outlet, so the vapor can lose as much heat as possible over a short distance. The coolant can also be taken out and chilled in the refrigerator before using.

Also, in combination with the mixing of the leaves (or tumbling), a smaller heater can then be used, thereby requiring less power and lengthening the battery life.

The current embodiment uses a rod heater, which typically uses much less power than using the following structures as heaters: (1) making the bottom of the bowl the heater, i.e. disc-shaped, or (2) the wall, i.e. cylinder-shaped. For other possible heater shapes, please see: http://zh4u.en.alibaba.com/; these examples are incorporated by reference. 3) Other possible structures:

To help the user visualize the mixing of the herbs during the mixing phase, the container glass wall and the plastic housing are designed to be transparent. Bong-style devices are typically made of glass, and some desktop vaporizers have clear enclosures as well. However, this is not a feature found on existing portable vaporizers.

In other embodiments, the bowl cap and mouthpiece can be one integrated unit and have a recess for the filter.

Some links to existing desktop/portable vaporizers
http://my-iolite.com/
http://en.wikipedia.org/wiki/Volcano_Vaporizer
http://www.vaporizer-info.com/vaporizer_types/
http://www.herbalvaporizerreview.org/

(1) An apparatus for vaporizing herbs and plants comprising: a housing, which contains a power source and an activation button for the power source and a vaporizing chamber;
  the vaporizing chamber has a heating element, which is connected to the power source, and at least one rotatable stirring element;
  the herbs and the plants are placed within the vaporizing chamber;
  a cap, a filter and a mouthpiece engage the vaporizing chamber;
  so that when the herbs and plants are heated by the heating element to form vapors, the at least one rotatable stirring element creates a concurrent mixing of the herbs and the plants during the vaporization, and the vapors from the herbs and the plants are able to pass through the filter and the cap and exit through the mouthpiece.

The apparatus as described above wherein the at least one rotatable stirring element is manually operated or motor operated; there is a first rotatable stirring element and a second rotatable stirring element; there is at least one roller, which engages the at least one rotatable stirring element.

The apparatus as described above wherein there is a cooling apparatus, which is placed in between the cap and the mouthpiece; the cooling apparatus comprises:
  a cooling apparatus body with a first end and a second end;
  the first end of the cooling apparatus body engages the cap;
  the second end of the cooling apparatus body engages the mouthpiece; and
  between the first and second ends of the cooling apparatus body, there is a condenser element or structure, which cools down the vapors from the herbs and the plants.

(2) An apparatus for vaporizing herbs and plants comprising: a housing, which contains a power source and an activation button for the power source and a vaporizing chamber;
  the vaporizing chamber has a moveable heating element, which is connected to the power source, and a moveable stirring element;
  the herbs and the plants are placed within the vaporizing chamber;
  a bowl cap, a filter and a mouthpiece engage the vaporizing chamber;
  so that when the herbs and plants are heated by the heating element to form vapors, the moveable heating and stirring elements create a concurrent mixing of the herbs and the plants during the vaporization, and the vapors from the herbs and the plants are able to pass through the filter and bowl cap and exit through the mouthpiece.

The apparatus as described above wherein the moveable stirring element is manually operated; wherein there is at least one roller, which engages the moveable stirring element; or wherein there is a cooling apparatus, which is placed in between the cap and the mouthpiece; the cooling apparatus comprises:
  a cooling apparatus body with a first end and a second end;
  the first end of the cooling apparatus body engages the cap;
  the second end of the cooling apparatus body engages the mouthpiece; and between the first and second ends of the cooling apparatus body, there is a condenser element, which cools down the vapors from the herbs and the plants.

(3) An apparatus for vaporizing herbs and plants comprising: a housing, which contains a power source and an activation button for the power source and a vaporizing chamber;

the vaporizing chamber has a rotatable heating element, which is connected to the power source, and a rotatable stirring element;

the rotatable stirring element has a first stirring element end and a second stirring element end; the first stirring element end lies within the vaporization chamber; the second stirring element end being able to manipulated through an opening in the housing;

the herbs and the plants are placed within the vaporizing chamber;

a bowl cap, a filter and a mouthpiece engage the vaporizing chamber;

so that when the herbs and plants are heated by the heating element to form vapors, the rotatable heating and stirring elements create a concurrent mixing of the herbs and the plants during the vaporization, and the vapors from the herbs and the plants are able to pass through the filter and bowl cap and exit through the mouthpiece.

The apparatus as described above wherein the rotatable stirring element is manually operated through the opening in the housing; wherein there is at least one roller, which engages the rotatable stirring element; or wherein there is a cooling apparatus, which is placed in between the cap and the mouthpiece; the cooling apparatus comprises:

a cooling apparatus body with a first end and a second end;
the first end of the cooling apparatus body engages the cap;
the second end of the cooling apparatus body engages the mouthpiece; and
between the first and second ends of the cooling apparatus body, there is a condenser element, which cools down the vapors from the herbs and the plants.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6. Any headings or labels within the text of the specification are for the convenience of the reader and are not intended to be limiting.

I claim:

1. An apparatus for vaporizing herbs and plants comprising:

a housing, which contains a power source and an activation button for the power source and a vaporizing chamber;

the vaporizing chamber has a heating element, which is connected to the power source, and at least one rotatable stirring element;

the housing has at least one roller, which engages the at least one rotatable stirring element;

the herbs and the plants are placed within the vaporizing chamber;

a cap, a filter and a mouthpiece engage the vaporizing chamber;

so that when the herbs and plants are heated by the heating element to form vapors, the at least one rotatable stirring element creates a concurrent mixing of the herbs and the plants during the vaporization, and the vapors from the herbs and the plants are able to pass through the filter and the cap and exit through the mouthpiece.

2. The apparatus of claim 1 wherein the at least one rotatable stirring element is manually operated.

3. The apparatus of claim 1 wherein the at least one rotatable stirring element is motor operated.

4. The apparatus of claim 1 wherein there is a first rotatable stirring element and a second rotatable stirring element.

5. The apparatus of claim 1 wherein there is a cooling apparatus, which is placed in between the cap and the mouthpiece; the cooling apparatus comprises:

a cooling apparatus body with a first end and a second end;
the first end of the cooling apparatus body engages the cap;
the second end of the cooling apparatus body engages the mouthpiece; and
between the first and second ends of the cooling apparatus body, there is a condenser element, which cools down the vapors from the herbs and the plants.

* * * * *